(12) United States Patent
Deck

(10) Patent No.: US 9,872,642 B2
(45) Date of Patent: Jan. 23, 2018

(54) MEDICAL DEVICE COMPRISING A MULTIPART HOUSING

(71) Applicant: Roche Diagnostics Operations, Inc., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 19 days.

(21) Appl. No.: 13/739,755

(22) Filed: Jan. 11, 2013

(65) Prior Publication Data
US 2013/0131468 A1  May 23, 2013

Related U.S. Application Data

(63) Continuation of application No. PCT/EP2011/061781, filed on Jul. 11, 2011.

(30) Foreign Application Priority Data

Jul. 12, 2010 (EP) .................................. 10169259

(51) Int. Cl.
| *A61B 5/1455* | (2006.01) |
| *A61B 5/145* | (2006.01) |
| *A61M 5/158* | (2006.01) |
| *A61M 5/172* | (2006.01) |

(52) U.S. Cl.
CPC ......... *A61B 5/14503* (2013.01); *A61M 5/158* (2013.01); *A61M 5/1723* (2013.01)

(58) Field of Classification Search
CPC ...................................................... A61B 5/1455
USPC ................................................... 600/310–344
See application file for complete search history.

(56) References Cited

U.S. PATENT DOCUMENTS

| 5,458,569 | A | * | 10/1995 | Kirk, III ............... A61M 37/00 604/20 |
| 5,800,420 | A | * | 9/1998 | Gross .................. A61K 9/0021 204/280 |
| 5,954,643 | A | * | 9/1999 | VanAntwerp et al. ....... 600/316 |
| 6,123,690 | A | | 9/2000 | Mejslov |
| 2001/0008963 | A1 | | 7/2001 | Alesi |

(Continued)

FOREIGN PATENT DOCUMENTS

| DE | 299 05 066 U1 | 9/1999 |
| EP | 2 077 128 A1 | 7/2009 |

(Continued)

*Primary Examiner* — Eric Winakur
*Assistant Examiner* — Marjan Fardanesh
(74) *Attorney, Agent, or Firm* — Bose McKinney & Evans LLP

(57) ABSTRACT

A medical device for carrying out at least one medical function, comprising at least one element that can be at least partially inserted into a body tissue of a user and further comprising at least one housing that can be placed on a skin surface of the user. The housing has a multipart design and comprises at least one functional component. The functional component can be connected to the insertable element. The housing further comprises at least one protective component. The protective component is designed to at least partially enclose the functional component. The protective component can be connected to the functional component, particularly after insertion of the insertable element.

23 Claims, 7 Drawing Sheets

(56) References Cited

U.S. PATENT DOCUMENTS

| | | | | |
|---|---|---|---|---|
| 2002/0169439 A1* | 11/2002 | Flaherty | ............ | A61M 25/0111 604/544 |
| 2006/0183984 A1* | 8/2006 | Dobbles et al. | .............. | 600/316 |
| 2009/0048563 A1 | 2/2009 | Ethelfield et al. | | |
| 2010/0004522 A1* | 1/2010 | Varela | ................ | A61B 5/14532 600/347 |
| 2010/0036445 A1* | 2/2010 | Sakai | ................... | A61N 1/0551 607/2 |
| 2012/0116190 A1* | 5/2012 | Iketani et al. | ................ | 600/309 |

FOREIGN PATENT DOCUMENTS

| | | | |
|---|---|---|---|
| WO | | 2003026728 A1 | 4/2003 |
| WO | | 2006077262 A1 | 7/2006 |
| WO | WO | 2006/077262 A1 | 7/2006 |

\* cited by examiner

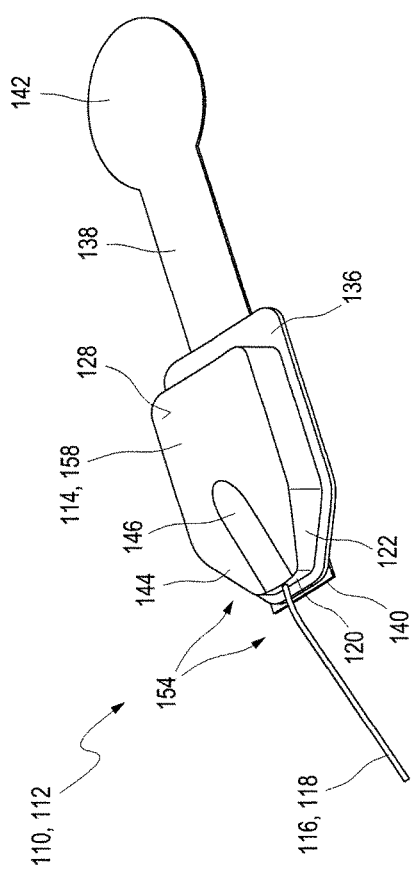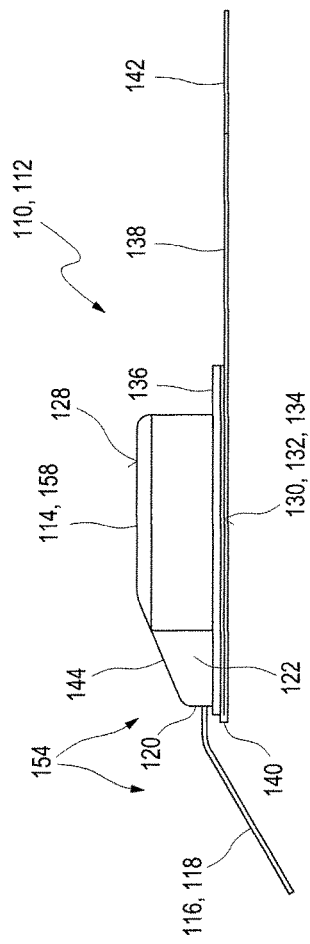

MEDICAL DEVICE COMPRISING A MULTIPART HOUSING

RELATED APPLICATIONS

This application is a continuation of PCT/EP2011/061781, filed on Jul. 11, 2011, which claims priority to EP 10 169 259.8, filed on Jul. 12, 2010, both of which are incorporated herein by reference in their entirety.

BACKGROUND

The invention relates to a medical device for carrying out at least one medical function, comprising a multipart housing and at least one element that can be inserted into a body tissue of a user. The invention further relates to a protective component for use in a medical device, and to a method for protecting a functional component of a medical device. Devices and methods of this kind are used particularly in the field of medical diagnostics, preferably in the field of home monitoring, particularly for monitoring a concentration of at least one analyte in a body fluid, for example blood or interstitial fluid, for example a glucose concentration and/or cholesterol concentration. Alternatively or in addition, however, other uses are also conceivable, for example uses in the field of medication, for example for administering medicaments such as insulin, particularly in the context of insulin pumps.

From the field of medical diagnostics or therapeutics, subcutaneous devices are known, i.e. devices that are designed to be inserted wholly or partially into body tissue, for example interstitial fatty tissue. This use is also generally referred to as insertion or implantation. Examples of such subcutaneous devices can in particular be found in the field of diagnostics, for example in the field of long-term monitoring of subjects or users, particularly in the context of "home monitoring" or else in a clinical context. Accordingly, medical devices can be equipped with at least one insertable element, for example an insertable sensor for qualitative and/or quantitative detection of at least one analyte (for example at least one metabolite) in the body tissue and/or a body fluid. Sensors of this kind can be based, for example, on electrochemical and/or optical detection principles. Alternatively or in addition, the medical device can also comprise other types of insertable elements, for example medication devices that can introduce specific active ingredients into the body tissue in a targeted and preferably dosed manner, for example, insulin. Without restricting further possible fields of application, embodiments are described below mainly with reference to medical devices having insertable sensors and/or with reference to insulin pumps.

In medical therapeutics and/or diagnostics, it is often necessary to detect one or more physical and/or chemical parameters in a body tissue of a user. Examples of such physical and/or chemical parameters are analyte concentrations of one or more analytes, for example glucose and/or cholesterol. For example, depending on the parameters that are detected, a medical treatment may be chosen, for example an administration of certain medicaments, and/or a different influence on the body or body functions of the subject. In particular, the prior art has disclosed numerous examples for qualitative or quantitative detection of one or more analytes by insertable subcutaneous sensors which preferably pass through a skin surface of a user and into a body tissue, for example fatty tissue. For example, insertable sensors can be based on electrochemical measurement principles and can comprise one or more chemical substances, also referred to as test chemicals, which specifically change one or more physically and/or chemically measurable properties in the presence of the at least one analyte to be detected. Examples of such test chemicals are enzyme-based test chemicals, which can be used in electrochemical sensors for example. Other measurement principles are based, for example, on optical properties, in which at least one test chemical changes at least one optically detectable property in the presence of the at least one analyte to be detected. In the context of this disclosure, reference may be made to all of the known measurement principles.

Medical devices of this kind with insertable sensors are generally used for long-term measurement, for example for continuous or intermittent measurement over a period ranging from several days, for example seven days, to several weeks, or even one or more months. During this time, the insertable sensors remain at least partially inside the body tissue. A technical and medical challenge generally lies in inserting the insertable sensor into the body tissue, for example the subcutaneous fatty tissue, in a way that causes the least possible pain. The insertion should take place in such a way that the insertable sensor can remain at least partially in the body tissue for a relatively long period of time, for example from several hours up to several days, and can thus supply measurement data continuously or intermittently. Therefore, the prior art has disclosed a number of insertion devices which, in addition to having the insertable element, for example the sensor, also comprise one or more insertion aids. For example, insertion aids of this kind can be designed wholly or partly as insertion needles and/or cannulas, into which the insertable element can be introduced or onto which the insertable elements can be applied, in order to be implanted into the body tissue therewith. The insertion aid can subsequently be removed again, with the insertable element, for example the sensor, remaining at least partially in the body tissue. Part of the insertable element can protrude from the body tissue, for example for later removal of the insertable element and/or for connection to control electronics.

Known medical devices in the form of long-term sensors (continuous monitoring, CM) generally have at least one insertable sensor, which is placed into the subcutaneous fatty tissue, and at least one peripheral module, which is generally applied directly or indirectly to a skin surface of the user. The at least one peripheral element generally has, for example, at least one electronic amplification system for amplifying sensor signals and/or for controlling the sensor. Alternatively or in addition, further modules can be contained, for example one or more radio modules, one or more energy reservoirs and one or more protective devices. In addition to these elements, the sensor is applied using the above-described insertion devices, also referred to as inserters, which are generally used only for the purpose of insertion and are generally removed thereafter from the medical device.

Directly after the insertion of the sensor or of the insertable element, bleeding can occur at the puncture site. This bleeding generally stops by itself after a few minutes and generally has no influence on the measurement quality of the medical device. However, under some circumstances, this bleeding poses a hygiene problem if the blood that has emerged is not removed and instead remains on the wound for the period during which the medical device is applied. Moreover, plasters are generally used to hold the peripheral elements on the skin surface, and the adhesive force of these plasters can be greatly limited by the blood wetting them.

Moreover, it is known from clinical studies that external mechanical influences such as pressure and tension can affect the technical measuring performance and signal quality of inserted long-term sensors. It is also known that constant relative movement between the sensor shaft, which protrudes through the skin surface, and the wound opening leads to irritation of the wound margins and thus causes the formation of fissures. The resulting wound irritation and possible inflammation also have a negative impact on the performance and the properties of the sensor.

However, conceivable design measures for preventing relative movements between the sensor shaft and the wound opening and for reducing mechanical influences on the surrounding tissue result in design problems or present a number of design challenges. For example, a simple mechanical protection, as could be used to overcome the listed problems, would lead to a spatial problem. A mechanical protection for preventing relative movements between sensor shaft and wound opening would have to stabilize the tissue located around the wound and mechanically connect it to the sensor base, i.e. the peripheral structural element, for example the functional component, on the skin surface. For this purpose, the smallest possible spaces between sensor base and wound are advantageous. However, small spaces entail considerable hygiene problems, since blood that emerges shortly after the insertion very quickly makes contact with a closely adjacent sensor base and spreads on account of capillary forces between sensor base and skin. For reasons of space, cleaning with swabs is also made difficult by the mechanical stabilization. Moreover, reducing the mechanical influences on the tissue in which the sensor is inserted would require the stabilization and coverage of the entire tissue area. However, in order to do this, the mechanical protection would need to have a size that corresponds at least to the length of the inserted sensor. A mechanical protection of this size, however, is very inconvenient during the insertion of the sensor, since insertion aids, for example of the kind described above, have themselves a spatial extent that would collide with the dimensions of conceivable protection devices.

SUMMARY

Embodiments incorporating this disclosure make available a medical device that has at least one insertable element and that avoids the disadvantages of known medical devices. In particular, a mechanical protection of the inserted element is to be ensured. At the same time, however, an insertion site should be easily accessible for cleaning, and the insertable element should be able to be easily inserted into a body tissue despite the mechanical protection.

In a first aspect of this disclosure, a medical device for carrying out at least one medical function is proposed. A medical function is to be understood generally as a diagnostic and/or therapeutic and/or surgical function. In particular, it can be a diagnostic function, i.e. a function for detecting at least one physical state of a user, for example a sensory function, in particular a sensor function for detecting at least one analyte in a body fluid. Alternatively or in addition, however, the medical function can also comprise, for example, a therapeutic function, i.e. a function which exerts at least one healing action and/or regulating action on the body and/or which can exert at least one influence on at least one physical state. In particular, it can be a medication function, i.e. a function which administers at least one medicament to the body, for example in a controlled and/or regulated manner, for example insulin or another medicament. Combinations of said medical functions are also possible, for example in which the medical device simultaneously integrates a diagnostic function, for example in the form of a measurement of a glucose concentration, and at least one medication function, for example in the form of an insulin medication, for example in the form of an insulin pump, in one and the same medical device, for example inside the same housing. The medical device can be designed in particular in the assembled state as an individual component and can in particular be designed to be worn on the body of the user, for example on a skin surface, for example in the abdominal area, in the arm area or in the back area of the user. For this purpose, the medical device can, for example, have a total volume of preferably not more than 200 ccm, in particular not more than 100 ccm, and particularly preferably not more than 50 ccm, or even not more than 10 ccm. The medical device can interact with other appliances, for example an external wireless data manager and/or control appliance connected to the medical device. Alternatively or in addition, the connection can, for example, also comprise a fluidic connection, for example a tube connection to a medication pump, e.g. an insulin pump. Various configurations are possible.

The medical device comprises at least one element that can be at least partially inserted into a body tissue of a user. This insertable element can be adapted to the at least one medical function. As has been explained above, an insertion is to be understood as a complete or partial introduction into a body tissue. This insertion is preferably done in such a way that part of the insertable element is guided through a skin surface of the user and into the body tissue. For example, as will be explained in more detail below, the insertable element can comprise at least one sensor for detecting at least one analyte in a body fluid, in particular an electrochemical and/or an optical sensor. Alternatively or in addition, the insertable element can also comprise an insertable part of a medication device, for example an insertable cannula which can cooperate with other parts of the medical device, for example with a medication pump, in particular an insulin pump. Combinations are also possible, for example a combination of at least one insertable sensor with at least one medication device.

Moreover, the medical device comprises at least one housing that can be placed on a skin surface of the user. The housing can, for example, be a constituent part of a base of the medical device or can form the base of the medical device, in which case the medical device thus comprises the insertable element and the base or is composed entirely of the insertable element and the base. As will be explained in more detail below, the insertable element can be connectable to the base or even rigidly connected to the base, such that the medical device is preferably designed in one piece in the assembled state.

According to this disclosure, it is proposed that the housing has a multipart design. Thus, the housing comprises at least one functional component, which is connectable to the insertable element. A functional component is to be understood in principle here as any component of the medical device that can be connected to the insertable element and for example, in the connected state, can cooperate mechanically and/or electrically and/or fluidically with the insertable element. For example, as will be explained in more detail below, the functional component can comprise at least one electronic and/or electromechanical and/or fluidic module, for example one or more electronic modules. For example, a control and evaluation circuit of the sensor can be contained wholly or partially in the functional component. In particular, the functional component can comprise at least one amplifier circuit and/or at least one potentiostat for an electrochemical sensor. Alternatively or in addition, further elements can be included in the functional component, for example one or more energy reservoirs, one or more memory elements, one or more communication modules, for example radio chips, or combinations of these and/or other elements. In particular, the functional component, with the modules contained therein, can function jointly with the insertable element, independently of further modules of the mechanical devices, or can comprise at least one function that can be carried out independently of further modules of the mechanical device, in particular of the housing of the mechanical device. For example, a sensor function and/or a medication function can be carried out alone by the insertable element and the functional component with the elements enclosed therein.

The functional component can be designed in one part. Alternatively, however, the functional component can in turn have a multipart design and can comprise, for example, two or more interconnectable functional component modules. For example, a first functional component module can be provided which is connectable or connected to the insertable element, and a second functional component module, which is in turn connectable directly or indirectly to the first functional component module, for example before, during or after the insertion. Thus, for example, the functional component itself can be subdivided into a disposable part, with the insertable element, and a reusable part. The reusable part can, for example, contain one or more reusable electronic modules and/or electromechanical modules and/or fluidic modules, for example one, several or all of the modules described above. The insertable element can be contained fixedly in the disposable part, or the insertable element can be connectable to the disposable part, for example by a plug or connector contained in the disposable part. Moreover, the disposable part can contain at least one electronic module and/or electromechanical module and/or fluidic module. A connection between the functional component modules can comprise, for example, a detachable connection, for example a plug connection. The connection can, for example, include or produce a mechanical and/or electrical and/or fluidic connection between the functional component modules.

The connection between the insertable element and the functional component can be rigid or releasable. It is preferably a physical connection of a solid nature. For example, the insertable element can be guided into the functional component and can there be connected rigidly thereto. In principle, however, another kind of connection is also possible, even in principle a wireless connection. The optional at least one module, which is enclosed by the functional component, can be integrated in the functional component in various ways. Thus, the at least one module, for example the at least one electrical and/or electronic and/or electro-mechanical and/or fluidic module, can be introduced into an interior of the functional component and can be enclosed, for example, by the functional component. Alternatively or in addition, however, the at least one module can also itself be a constituent part of the functional component, for example by being integrated in the functional component. Thus, for example, the wall of an electronic chip housing can be integrated in the functional component, for example by encapsulation of this chip housing by injection molding, or by its being enclosed in some other way by a material of the functional component, such that it itself becomes a constituent part of a wall material of the functional component. Various configurations are conceivable.

As has been mentioned above, provision is made, according to this disclosure, that the housing has a multipart design. This means that the housing comprises, in addition to the at least one functional component, one or more further elements which together form the housing. It is accordingly proposed that the housing also has at least one protective component. A protective component is to be understood as a component of the housing that provides protection for the functional component and/or the insertable element, in particular mechanical protection, for example against compressive loads and/or tensile loads and/or flexural loads. In particular, protection can be made available against a compressive, tensile or flexural load of the element inserted into the body tissue.

The protective component is designed to at least partially enclose the functional component. As will be explained in more detail below, enclosure is understood as meaning that the protective component is designed such that in at least one dimension, for example in at least one plane, for example parallel to a skin surface of the user, it completely surrounds or borders the functional component, or does so at least about an angular range, it being possible for said surround to be complete or partial. Possible configurations are described in more detail below.

The protective component is designed to be connected to the functional component. This connectability can in particular be configured in such a way that it can even take place after insertion of the insertable element. Thus, insertion of the insertable element can first take place, followed by a connection of the protective component to the functional component. A connection between the protective component and the functional component is understood as these components being joined together to form a common component. This connection can be made directly or indirectly, such that the functional component and the protective component can touch each other in the connected state. However, a contact-free connection is also possible, for example in which at least one gap is formed between the functional component and the protective component and/or in which the connection is made via at least one intermediate element. For example, a common plaster and/or even the skin of the user can act as the intermediate element, for example in the form of a bridge. The functional component and/or the protective component can be designed in such a way that this connectability can be guaranteed. For example, one or more connection elements can each be provided on the functional component and/or the protective component. For example, an outer shape of the functional component can also be designed in such a way that it can be fitted at least partially into a seat of the protective component. In the context of this disclosure, "connectable" is therefore to be understood as meaning that the functional component and the protective component can be combined, the connection resulting in the formation of the device or a part thereof, and, in the connected state, the functional component and the protective component are arranged in a predetermined orientation and/or arrangement with respect to each other, such that the protective component can perform its protective function.

This common component can, for example, be a base of the medical device. For example, this base can be placed completely or partially and directly or indirectly onto a skin surface of the user. For example, in the connected state, an outer shape of the housing can be defined at least in one plane, for example a plane parallel to the skin surface, by the protective component, such that the protective component can define the outer dimensions of the housing in at least this sectional plane. It is preferable, but not essential, that the protective component touches the functional component in the connected state. The connection between the functional component and the protective component can be made directly or, alternatively or in addition, it can also be provided by other elements, for example by one or more connection elements, of which examples are given in more detail below.

The medical device can be designed such that the protective component encloses the functional component in such a way that at least one insertion site is accessible where the insertable element passes through the skin surface of the user. This accessibility can, for example, permit access from above, from a side of the base or housing opposite the skin surface, for example access with a cotton bud or another cleaning device, for example for cleaning and/or disinfecting the insertion site and/or for the purpose of observing the insertion site. For example, with the protective component connected to the functional component, a free space can remain around the insertion site, for example a free space through which a user can, from the outside, look through the protective component and the functional component and observe the insertion site or can clean this insertion site and/or treat it in some other way. Generally, the device can be designed in such a way that the insertion site is visually accessible. For example, this free space can have a lateral dimension, for example a diameter (for example a circle diameter and/or another variable characterizing a lateral extent), and/or an edge length of at least 2 mm, preferably at least 3 mm and particularly preferably at least 5 mm, or even at least 7 mm or even at least 10 mm. For example, a free space can be provided having a lateral extent of 2 mm to 20 mm, particularly of 3 mm to 15 mm, and particularly preferably of 5 mm to 15 mm. In particular, in a direction parallel to the skin surface, for example in the plane of the skin surface, the insertion site can be completely surrounded by the housing, for example in a ring shape or frame shape. The free space can in principle have any desired cross section, for example an oval, round, polygonal or other cross section.

In order to be able to provide particularly effective stabilization of the medical device when the insertable element is inserted into the body tissue, and for example to reduce a compressive load and/or tensile load and/or weighing load of the insertable element, it is particularly preferable if the insertion site is arranged substantially centrally with respect to a contact face of the housing on the skin surface. Substantially centrally is to be understood as meaning that the insertion site, i.e. a point or an area where the insertable element passes through the skin surface when the medical device is used in the manner intended, is arranged substantially in the centroid of the contact face. For example, the insertion site can be arranged in the centroid of the projection of the optional free space onto the skin surface, or the centroid of the optional free space onto the skin surface can be arranged substantially in the centroid of the contact face. An arrangement "substantially in the centroid" is generally to be understood as meaning that the deviation of the points from the centroid is in no direction more than 50% of the maximum lateral extent (for example of a diameter) of the contact face, preferably not more than 20%, particularly preferably not more than 10%, and in particular not more than 5%.

As has been mentioned above, the insertable element can in particular comprise a sensor for detecting at least one analyte in a body fluid. In particular, this can be an electrochemical sensor and/of an optical sensor, for example a sensor for qualitative and/or quantitative detection of blood glucose and/or cholesterol. Alternatively or in addition, however, the insertable element can also comprise at least one constituent part of a medication device. For example, at least one constituent part of an insulin pump, for example at least one cannula. This cannula can, for example, be flexible or also rigid and can, for example, comprise a tube attachment, in order to be connected by a flexible tube to a pump, for example to a medication pump and in particular an insulin pump.

As has been explained above, the protective component can in particular be reversibly connectable to the functional component. Accordingly, for example, the functional component can be designed, along with the insertable element, as an element that can be used over a relatively long period of time, whereas the protective component can be replaced at regular or irregular intervals, for example in order to improve the hygiene of the medical device as a whole. The protective component can enclose the functional component particularly in the shape of a frame. For example, in a plan view looking perpendicularly with respect to the skin surface in the assembled state, i.e. with the protective component connected to the functional component, it is possible to see both the functional component and also the protective component and preferably also an insertion site. This means that the protective component preferably encloses the functional component only in the lateral direction, i.e. in a plane parallel to the skin surface, while an enclosure perpendicular to this plane, i.e. in a direction perpendicular to the skin surface, is likewise possible in principle but is not preferred. The functional component and the protective component preferably have substantially the same height in a direction perpendicular to the skin surface. For example, the maximum heights of these components can deviate from each other by not more than 50%. However, other configurations are also possible in principle.

It is particularly preferable if the functional component has a long side, in which case the protective component encloses the functional component at least along the whole of the long side. However, it is particularly preferable if the protective component protrudes beyond the long side of the functional component, for example in order also to enclose a projection of the insertable element, for example of the sensor, onto the skin surface. Generally, for example, an outer edge of the protective component can completely enclose a projection of the functional component and of the insertable element onto the skin surface of the user. This means that, even in the inserted state of the insertable element, the projection of the insertable element onto the skin surface of the user is completely enclosed by the housing, i.e. either by the functional component or by the protective component.

As has been mentioned above, the functional component preferably has at least one function, for example the function of receiving and/or evaluating signals from the sensor and/or a fluidic function, for example a pump function and/or another electromechanical and/or electrical and/or fluidic function. It is particularly preferable if at least one function of the functional component can be carried out independently of the presence of the protective component. In particular, this can be at least one medical function, which can be carried out by the functional component in cooperation with the insertable element, preferably in the inserted state. For example, this can be a detection function for detecting at least one analyte in the body fluid and/or a medication function. This means that, in this context, the protective component can be removed as and when desired from the functional component, without disrupting the at least one medical function, or that the medical function can already be carried out before the protective component is connected to the functional component. Alternatively or in addition, however, and as is explained below, the functional component can likewise have at least one function, for example an independent function. Alternatively or in addition, the protective component can also have at least one function that is carried out in cooperation with the functional component. Various configurations are possible, and examples of these are explained in more detail below.

As has been mentioned above, the protective component is connectable to the functional component. This connection can be made in various ways. In particular, the protective component can be designed to be connected to the functional component with a form fit and/or force fit. For example, a form fit and/or force fit can be obtained by simple enclosure, in which case the protective component for example comprises at least one opening, which is adapted to the functional component and which, for example, can be adapted in at least one dimension to an outer dimension of the functional component, so as to permit simple enclosure. If appropriate, the opening can also have slightly smaller dimensions and be made flexible and/or deformable, such that enclosure results in a form fit and/or force fit. However, as an alternative or in addition to a form fit and/or force fit, other types of connection are also possible, for example connections by integral bonding.

As has been mentioned above, the protective component can in particular have at least one opening into which the functional component can be completely or partially fitted. In particular, this can be a through-opening, i.e. an opening that extends all the way from a side of the protective component facing toward the skin surface to a side of the protective component facing away from the skin surface. In particular, it is preferable if a shape of the opening is adapted at least in parts to an outer shape of the functional component, for example corresponding exactly to the outer shape of the functional component, having only slight play (for example play of not more than 1 millimeter or 0.5 millimeter), or even being slightly smaller than the outer shape of the functional component, and, in the latter case, a deformable configuration of the walls of the opening is preferred, for example an elastic and/or plastic deformability. In particular, the opening can be configured such that, with the protective component connected to the functional component, a free space accessible from the outside remains inside the opening around an insertion site where the insertable element passes through the skin surface of the user. For example, as has been mentioned above, this free space can have a lateral dimension, for example a diameter and/or an edge length, of at least 2 mm, in particular 3 mm, and particularly preferably at least 5 mm. However, it is particularly preferable for the lateral dimension not to exceed 10 mm, preferably not to exceed 7 mm. For example, the opening, in particular the through-opening, can be divided into at least two areas, for example in a plane parallel to the skin surface. Thus, at least a first area can be provided, in which the functional component is received or can be received, for example with a form fit or force fit, and another area, namely the free space or an area comprising the free space. The insertable element can be connected or is connected to the functional component on that side of the functional component facing toward the free space. For example, this can be a front face of the functional component. In a plane parallel to the skin surface, for example, the functional component can have a round, oval or polygonal shape, for example a rectangular shape. For example, the insertable element can be connected or is connected to the functional component on a narrow front face of a rectangular functional component, for example by means of the insertable element being guided on this side into the interior of the functional component. The functional component can in particular be asymmetrical in shape and/or the opening can be configured in such a way that the side connectable to the insertable element always faces toward the free space when the functional component is connected to the protective component. In particular, the configuration of the opening and/or the shape of the functional component can be such that the functional component is not rotatable inside the opening.

The housing can in particular be at least partially deformable, preferably flexible. In particular, the protective component can be made from at least one flexible material, in other words can be made flexible at least in some areas. The functional component can likewise be made flexible in principle, but it is preferably made from a harder material than the protective component. Accordingly, the enclosing protective component can be softer than the centrally disposed functional component, such that the functional component can provide greater mechanical protection for modules received in the functional component. The protective component can, for example, have a Shore A hardness of 20 to 70, preferably of 30 to 50. The functional component can in particular have a Shore A hardness of 30 to 100, preferably of 40 to 80. The protective component and the functional component can in particular also comprise at least one biocompatible and skin-friendly material or can be made completely or partially from such a biocompatible and skin-friendly material. The protective component and/or the functional component can in particular be made completely or partially from a silicone and/or a polyurethane.

The functional component can in particular be dimensioned and/or configured in terms of its outer shape in such a way that insertion of the insertable element is possible when the insertable element is connected to the functional component. For this purpose, the insertable element can, for example, be connected to the functional component on one side of the functional component. For example, this side can be a front face, for example a narrow face of the functional component. Thus, the connection between the insertable element and the functional component is preferably not made on a side of the functional component facing toward the skin surface, but instead on another side of the functional component. For example, this connection can be made on a surface which is oriented substantially perpendicularly with respect to the skin surface. For example, a front face of the functional component. As has been mentioned above, the connection can be rigid or also releasable. It is particularly preferable if the functional component comprises at least one recess on the side where the insertable element is connected or can be connected to the functional component. For example, the functional component can comprise at least one depression which faces toward this side and which extends obliquely with respect to the skin surface in the direction of this side, particularly a groove facing toward the insertable element, in order to facilitate insertion. The depression, for example a furrow or groove, can extend, for example, at an angle of 20° to 70° with respect to the skin surface, for example at an angle of 25° to 55°, and particularly preferably at an angle of 45°. Arranging the connection between the insertable element and the functional component on one side of the functional component greatly facilitates the insertion of the insertable element, in contrast, for example, to insertion underneath the functional component. At the same time however, the connection of the protective component to the functional component, which connection is preferably made after the insertion, can ensure that, as has been mentioned above, a mechanical protection is ensured all the way around the insertion site. It is thus possible to solve the above-described technical dilemma of being able to make available a space for an insertion, for example an insertion aid, since only the functional component is arranged in the area of the insertion site, and preferably alongside the insertion site, during the insertion. Subsequently, that is to say after removal of the insertion aid for example, the protective component can be connected to the functional component and, for example, completely enclose the insertion site, so as to ensure an all-round protection of the insertion site and preferably also of the insertable element introduced into the body tissue. The at least one optional depression of the functional component can facilitate the functionality of the insertion aid and, for example, can be designed in a continuation of the insertion direction inside the body tissue.

The functional component and also the protective component may rest directly on the skin surface in the connected state. For this purpose, both the functional component and also the protective component can each have at least one contact face. The contact face of the functional component can at least partially enclose, preferably completely enclose, the contact face of the protective component. The contact faces can be arranged in such a way that they rest on the skin surface when the medical device has been placed onto the skin surface. The functional component and the protective component can each have at least one self-adhesive surface facing toward the skin surface, for placing on the skin surface and for connecting to the skin surface. For example, these self-adhesive surfaces can be designed in the form of plasters or in the form of one or more adhesion layers that can be applied to the surfaces. The functional component and the protective component can each have separate liners that can be pulled off when they are in the state applied to the skin surface. A liner is to be understood as a protective film which itself is preferably non-adhesive, of the kind known for self-adhesive surfaces from the field of plaster technology. The liners can preferably be folded back at an edge of the self-adhesive surface, such that a pull-off tab is formed. This pull-off tab can initially extend parallel to a part of the liner applied to the self-adhesive surface, for example below this part, between the skin surface and the part applied to the self-adhesive surface. The pulling-off direction can then be arranged parallel to the self-adhesive surface, such that the pulling-off process begins at the folded-back edge and, therefore, the liner can be reliably removed from the self-adhesive surface.

The functional component and the protective component may each have their own self-adhesive surfaces, which are not connected to each other. Alternatively, however, the self-adhesive surfaces can also be connected to each other or can be designed as at least one common self-adhesive surface. For example, one common plaster can be used for the functional component and the protective component. For example, the plaster of the functional component can be of such a size that the protective component can also be applied thereto, or vice versa.

As has been mentioned above, the protective component can be designed as a completely inert component which does not itself have any functionality other than the function of mechanically stabilizing and protecting the functional component and/or the sensor. However, the protective component can also itself have at least one further functionality. For example, the protective component can have at least one passage, particularly for the electrical contact of the functional component. For example, this passage can comprise at least one simple opening for passing at least one cable and/or of a plug through the protective component to the functional component.

As has been mentioned above, the housing comprises the at least one protective component and the at least one functional component. In addition, the housing can comprise further structural elements. For example, the housing can have at least one protective covering. The protective covering can in particular be made at least partially transparent, for example in order to ensure that the insertion site can be observed visually. The protective covering can be designed as a separate component. Alternatively or in addition, however, the protective covering can also be completely or partially a constituent part of the functional component and/or of the protective component. For example, at least one protective covering can be provided which can be applied over the protective component and the functional component and, in the applied state, at least partially covers the protective component and the functional component on a side facing away from the skin surface. For example, the protective covering can be designed as a self-adhesive plaster, in particular as a transparent plaster. It is thus possible to ensure that an insertion site, for example, can be seen from outside through the self-adhesive plaster, for example in order to be able to detect inflammations, for example. Alternatively or in addition, the at least one protective covering can also be at least partially integrated in the protective component and/or the functional component. For example, the protective covering can be designed as a cap that can be a constituent part of the protective component. For example, as has been mentioned above, the protective component can have at least one seat into which the functional component can be fitted, i.e. at least one opening. However, this opening does not necessarily have to extend all the way from the skin-surface side to the opposite side of the protective component. Thus, the opening can simply extend from the skin-surface side into a body of the protective component, for example in the form of a depression, particularly in the form of a depression adapted to the functional component. On the side facing away from the skin surface, the rest of the protective component can then completely or partially span the functional component and form a protective covering (for example connected rigidly to the protective component) of the functional component. The protective covering can in particular be made transparent in this area.

As has been mentioned above, the functional component can have at least one medical function, i.e. can be designed to carry out at least one medical function. The functional component can in particular enclose at least one electronic and/or electromechanical and/or fluidic functional module that is connectable, in particular connected, to the insertable element. For example, this can be an electronic module that can be received completely or partially in the functional component. For example, it can be an amplifier or an amplifier module, for example a primary amplifier with high input impedance. Alternatively or in addition, at least one potentiostat for electrochemical measurements can be provided. Again alternatively or in addition, the at least one functional module can, for example, comprise at least one pump, for example a medication pump.

As has been mentioned above, the protective component can be designed in particular as an inert protective component, which preferably only provides mechanical protective functions. However, it is likewise possible that the protective component itself also has at least one function, for example an electrical function, an electronic function, a data storage function, an energy supply function, a communication function, a measuring function, a medication function, an actuator function, a sensor function or a combination of these and/or other functions. For example, the protective component can enclose at least one electronic and/or electromechanical and/or fluidic functional module, for example analogously to the above-described design of the functional component. The functional modules of the functional component and of the protective component can be designed independently of one another but can also interact. For example, the functional component can comprise at least one electronic module, which interacts with an insertable element in the form of a sensor. The protective component can comprise at least one fluidic functional module, for example in the form of a medication pump, which can interact with a further insertable element, for example a cannula, in order to carry out a medication function. Thus, in addition to the at least one insertable element that is connectable or connected to the functional component, at least one further insertable element can be provided that is connectable and/or connected to the protective component. For example, this can again include one or more of the above-described insertable elements, such that, for example, a sensor function can also be combined with a medication function or with another actuator function, wherein the functions can be shared for example between the protective component and the functional component. The protective component can in particular enclose a functional module that can be chosen from: an energy reservoir, in particular a battery; a data storage element, in particular a non-volatile data storage element; a communication module for wireless and/or wired communication with at least one external appliance, in particular a radio module; a medication pump. Combinations of these and/or other functional modules are also conceivable.

Furthermore, the device can comprise one or more further functions and/or functional modules. For example, at least one absorbent module can be provided in the protective component and/or in the functional component, for example in order to absorb body fluid that emerges at the insertion site. It is particularly preferable if an absorbent module of this kind is provided in the protective component, since the latter can generally be easily exchanged and disposed of. The absorbent module can, for example, comprise at least one absorbent textile material and/or at least one absorbent paper material. Alternatively or in addition, other absorbent materials can also be used, for example absorbent, sponge-like materials, for example from a hydrophilic synthetic substance or natural substance.

As has been mentioned above, the functional component and the protective component are connectable to each other, preferably exclusively mechanically. Moreover, however, the housing can also have at least one electrical interface between the functional component and the protective component, in which case the interface can be designed in such a way that, when the connection between the functional component and the protective component is made, an electrical connection can also be produced between the functional component and the protective component. For example, an electrical plug connection can be produced, which is preferably reversible. In this way, for example, functional modules inside the protective component can communicate with functional modules inside the functional component and/or can exchange data and/or energy. However, as has been stated above, it is particularly preferable if at least one function of the functional component can be carried out independently of the presence of the protective component, such that, for example, an energy supply is provided inside the functional component without the presence of the protective component, for example by means of an energy reservoir. Alternatively, however, electrical energy can also be made available by the protective component.

In a further aspect of this disclosure, at least one protective component is proposed for use in a medical device with at least one functional component and at least one element that can be inserted into a body tissue of a user and can be connected to the functional component. In particular, this can be a medical device according to one or more of the above-described embodiments, such that, for preferred configurations of the protective component, reference can be made to the above description and to the optional features set forth there relating to the protective component. However, another configuration is also possible in principle. The protective component has at least one contact face for placing onto a skin surface of the user. The protective component is connectable to the functional component, the protective component having at least one seat with at least one opening, the seat being designed in such a way that the functional component can be fitted into the seat. The protective component at least partially encloses the functional component in the connected state. For example, one functional component and one or more protective components can also be combined to form a kit and can be supplied as a kit. The kit can also comprise one or more insertable elements of an identical or different kind. In particular, as has been described above, the protective component in the medical device can be designed to be exchangeable, such that, for example during the operation of the medical device, the protective component can be replaced by a new protective component, for example for hygiene purposes.

In a further aspect of this disclosure, a method is proposed for protecting at least one functional component of a medical device that is placed onto a skin surface of a user, and for protecting at least one element that is connected to the functional component and is insertable, in particular inserted, into a body tissue of the user. Here too, a medical device according to one or more of the above embodiments can again be used, such that, for optional configurations of the medical device, reference can be made to the above description. In particular, a protective component according to these teachings can be used. In the proposed method, at least one protective component is connected to the functional component, wherein the functional protective component at least partially encloses the protective functional component.

The method can in particular be used on an arrangement in which the insertable element is already inserted into the body tissue and connected to the functional component. The insertion can be a constituent part of the method but is preferably not a constituent part of this method. In an arrangement of this kind, a liner can optionally be removed from a self-adhesive surface of the functional component, such that the functional component adheres to the skin surface. Thereafter, at the same time or beforehand, the protective component can be connected to the functional component, for example by introducing the functional component into a seat of the protective component having at least one opening, preferably a through-opening. Thereafter, a liner can optionally be removed from a self-adhesive surface of the protective component, such that the protective component is fixed on the skin surface and is preferably also fixed spatially with respect to the functional component, by the connection to the functional component and/or the adherence to the skin surface. In a further method step, a protective covering can optionally be applied over the protective component and the functional component, for example a flexible and/or deformable protective covering, for example in the form of a transparent film, in particular a self-adhesive film, preferably in the form of a transparent plaster. This protective covering can itself be affixed to the skin surface in an area around the functional component and/or the protective component or can simply be affixed to the functional component and the protective component. Various configurations are possible.

The proposed devices and the proposed method have many advantages over known devices and methods. In particular, according to this disclosure, a sensor base, which interacts with the insertable element, can be divided into several individual parts, which can be assembled one after another and can also optionally be made from different materials. These individual parts, which include the functional component and the protective component, can be adapted in size and shape to the respective work step. In particular, after completion of the insertion procedure, the assembled individual parts, i.e. the functional component and the protective component and optionally further components, can form one unit. At the time of the insertion, the sensor base can consist solely of an extremely small part, namely the functional component, which can meet only the most necessary mechanical requirements and can be made from an optional material for this purpose. The material of the functional component can, for example, be moisture-proof and/or can have electrically shielding properties and/or can have a high degree of mechanical strength. Because of the small overall size of the functional component, an optimal insertion device can be embodied for insertion of the insertable element. Moreover, optimal access to the wound, i.e. to the insertion site, is possible, as a result of which the latter can be optimally observed and cleaned. Protective functions for electronic components can be provided by suitable housing materials of the functional component, which materials must at least have no elasticity. After the insertion, for example, a mechanical protection can then be assembled in the form of the protective component, which can connect to the functional component by means of one or more mechanical connections and optionally also by means of one or more interfaces. This protection can be provided in an ideal size and from special materials, since no compromise has to be made with the insertion device or the electronics housing of the functional component. For example, a mechanical protection extending in a ring shape around an insertion site and/or insertion device can be provided by the protective component. Possible materials for the protective component are, in particular, elastic silicones or other skin-friendly materials. The connection of the protective component to the functional component can be made, for example, by means of a force fit and/or form fit. If the wound in the area of the insertion site bleeds during the period of use, it is generally sufficient to remove the outer mechanical protection provided by the protective component and clean and/or monitor the wound. The actual medical function, for example the actual sensor or the insertable element, can remain in place, and the spatial conditions are still ideal for the cleaning and monitoring.

After the cleaning and/or monitoring, the protection can be fitted in place again. The cleaning can be carried out before the connection of the protective component to the functional component and/or just after the production of this connection.

Moreover, it is also possible, in addition to the at least one mechanical function, to share other system requirements between the separate components of the housing. For example, it is possible to accommodate an antenna, an energy reservoir or a cable strain relief in various individual parts, for example in the functional component and/or in the protective component.

The possibility of performing step-by-step assembly and connection of the individual parts also permits the spatial integration of independent secondary systems into a base of the medical device, for example into a sensor base, in particular a sensor base of a continuously measuring sensor. For example, it is possible to integrate a medication function, for example an infusion catheter for insulin dosing and/or an insulin pump or parts of said devices, into separate components. The individual parts can be developed and produced separately and are, for example, joined together by the customer. For example, the medical device can provide a first insertable element in the form of a sensor, for example a continuously measuring sensor, which is coupled or can be coupled to the functional component, in combination with a second insertable element in the form of an infusion catheter, which is coupled to the protective component, wherein for example the protective component has at least one medication function, for example a fluidic and/or electromechanical module for medication, for example an insulin pump or another type of medication pump.

The medical device can, for example, be used such that the at least one insertable element is first inserted into the body tissue. For example, this can be a sensor. Alternatively or in addition, one or more further insertable elements can be inserted, for example a cannula of a medication pump, for example an insulin pump. According to this disclosure, a protective device can be made available for the already inserted sensor or the already inserted element. For example, the functional component can first be coupled to the insertable element or can already be coupled to the functional component during the insertion. After the insertable element has been introduced into the body tissue with the aid for example of an insertion aid, and preferably after the functional component has been connected to the skin surface, for example via the self-adhesive surface and/or a plaster, the protective component is then preferably connected to the functional component. This can be done, for example, by the protective component being pushed over the functional component in such a way that the insertion site, for example the puncture site, is still visible and, for example, accessible to the user or a physician or nursing personnel, for example in order to remove excess blood or to perform long-term observation of the insertion site. The purpose of the protective component can be, in particular, to provide mechanical protection in order to stabilize the position of the insertable element during the period of use, for example during a 7-day period of use of the sensor, and to shield the insertable element from impacts and movements of the skin. It has proven particularly expedient if the insertion site is arranged in the center of the housing, that is to say centrally with respect to the surface on which the housing rests on the skin surface. The protective component can be designed, for example, in the shape of a ring, for example a round and/or oval swim ring, which, for example in the form of a watertight plaster, acts above the insertable element, for example the sensor. In addition, it can be advantageous if the entire position of the insertable element and/or of the functional component is covered by the protective component. Preferred embodiments for the protective component are embodiments with flexible materials, in contrast to the preferred hard materials that can be used for the functional component. The protective component can preferably be removed at any time, that is to say can be decoupled in particular from the function of the functional component, in cooperation with the insertable element, for example from a sensor function of the functional component and of the insertable sensor. In the case of long-term use of the insertable element, the protective component, for example, can be made exchangeable for reasons of hygiene.

BRIEF DESCRIPTION OF THE DRAWINGS

Further details and features of the invention will become evident from the following description of preferred illustrative embodiments, particularly in conjunction with the dependent claims. Here, the respective features can be realized either singly or severally in combination with one another. The invention is not restricted to the illustrative embodiments. The illustrative embodiments are depicted schematically in the figures. The same reference numbers in the individual figures designate identical elements or elements that have an identical function or that correspond in terms of their functions.

FIGS. 1A and 1B show different views of a functional component and of an insertable element connected to the functional component before insertion into the body tissue;

DETAILED DESCRIPTION

Figure 2:
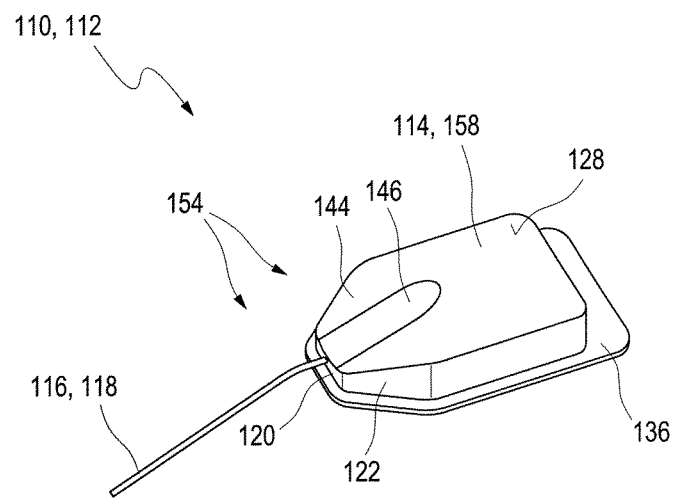
FIGS. 2A and 2B show different views of the assembly according to FIGS. 1A and 1B after detachment of a liner and after insertion into a body tissue.
Figure 2:
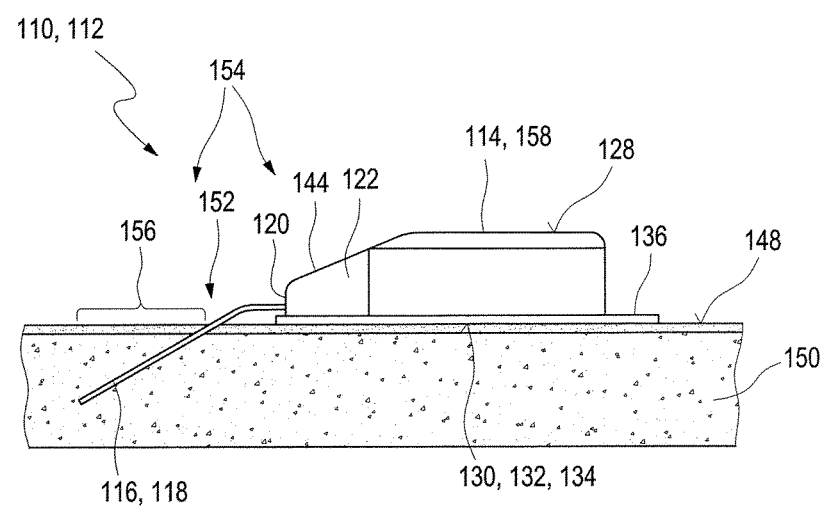

The embodiments of this disclosure described below are not intended to be exhaustive or to limit the invention to the precise forms disclosed in the following detailed description. Rather, the embodiments are chosen and described so that others skilled in the art may appreciate and understand the principles and practices of this disclosure.

In FIGS. 1A to 5B, different components of a medical device 110 for carrying out at least one medical function are shown in different views and in different stages of assembly. In the illustrative embodiment shown, the medical device is a sensor device 112, which can be used for long-term measurement of one or more medical parameters, in particular for long-term measurement of one or more analytes in a body tissue and/or a body fluid, for example for long-term monitoring of a glucose concentration. At the same time, FIGS. 1A to 5B show various possible stages of an illustrative embodiment of a method according to this disclosure for protecting at least one functional component 114, placed on a skin surface of a user, and for protecting an insertable element 116 that is connected to the functional component 114 and, in the illustrative embodiment shown, is designed as an insertable sensor 118. Alternatively or in addition, however, other types of insertable elements can also be provided.

As is shown in FIG. 1A, the functional component 114 can be designed particularly in one part. As has been described above, however, the functional component 114 can in principle also have a multipart design and can, for example, comprise several functional component modules, for example a disposable and a reusable. In the illustrative embodiment shown, the functional component 114 is substantially cuboid, with a front face 120, and with beveled edges 122 directed toward this front face 120. As a result of the beveled edges 122, the front face 122 represents the narrowest side of the contour of the functional component 114 in the illustrative embodiment shown, in a top view of the functional component 114 in FIG. 1B. In the views according to FIGS. 1A and 1B, the insertable element 116 is connected to the functional component 114 at the front face 120. For example, the insertable element 116 can be connected directly to the functional component 114 or guided into the interior of the functional component 114 and connected there, for example, to a functional module 124, for example a control and evaluation circuit, for example with at least one potentiostat and/or at least one high-impedance measurement amplifier, which functional module 124 cannot be seen in FIGS. 1A and 1B but is visible through the medical device 110 in a cross-sectional view according to FIG. 5B. This at least one functional module 124 can be contacted for example via at least one interface 126, as can also be seen from FIG. 5B. This interface 126 can, for example, comprise a cable duct and/or a plug and/or similar for electrical contact of the functional module 124 and/or for energy supply and/or for controlling the functional module 124.

As can be seen in FIG. 1B, the functional component 114 has a top 128 and an underside 130. During operation, the top 128 faces away from a skin surface of a user, whereas the underside 130 faces the skin surface. The underside 130 is accordingly designed as a contact face 132 of the functional component 114. In the illustrative embodiment shown, this contact face 132 is designed as a self-adhesive surface 134, for example by means of a self-adhesive plaster 136, as can be seen from the perspective view according to FIG. 1A. In the illustrative embodiment shown, the self-adhesive surface 134 is protected by a pull-off liner 138, i.e. a protective pull-off film that completely covers the self-adhesive surface 134 in the unused state. By way of example, this liner 138 is bent back at an edge 140 and returned parallel to itself, such that a pull-off tab 142 is formed at the end opposite the front face 120.

The assembly according to FIGS. 1A and 1B comprising the functional component 114 and the insertable element 116 is applied, in the state shown, to a skin surface of a user, and the insertable element 116 is inserted into the body tissue of the patient by means of a suitable insertion device or inserter (not shown). To make placement of the insertion device spatially easier during the insertion, for example with a cannula in which the insertable element 116 is wholly or partially received, the top 128 of the functional component 114 is beveled toward the front face 120. In the illustrative embodiments shown in FIGS. 1A and 1B, the insertable sensor 118 is also oblique with respect to the underside 130, such that it penetrates into the body tissue at an angle during insertion, for example at an angle of ca. 45°. The insertable sensor 118 can, for example, also be curved. For example, the insertable sensor can first of all be substantially rectilinear or have a first curvature outside the body tissue, and it can then penetrate into the body tissue at an angle, for example said angle of 45°. Inside the body tissue, the insertable sensor 118 can then extend, for example, in another direction and/or with another curvature or also, for example, rectilinearly and/or at another angle with respect to the skin surface, compared to its extent outside the body tissue. Thus, for example, the insertable sensor 118 inside the body tissue can extend at a shallower angle with respect to the skin surface than it does outside the body tissue. Thus, for example, the insertable sensor 118 can extend inside the body tissue at an angle of less than 20° with respect to the skin surface, or even substantially parallel to the skin surface. The bevel 144 of the top 128 toward the front face 120 can substantially follow the angle of the insertable sensor 118 with respect to the skin surface outside the body tissue. Moreover, the functional component 114 can have an elongate depression 146, for example a groove, in which the insertion needle or another part of the insertion device can extend and which likewise, in terms of its angle, can substantially follow the angle of the insertable element 116. In this way, the functional component 114 can be designed such that it does not spatially impede the insertion or only minimally impedes the insertion.

After placement on the skin surface and after the insertion, the liner 138 can be removed, for example by means of the pull-off tab 142 being pulled in a direction away from the edge 140. The self-adhesive surface 134 now adheres to the skin surface. This is shown in FIGS. 2A and 2B, where FIG. 2A shows a plan view of the sensor assembly with the functional component 114 and the insertable element 116 after the liner 138 has been pulled off, and where FIG. 2B shows a side view of the sensor assembly, together with the skin surface 148 and a cross section through the body tissue 150. It will be seen from FIG. 2B that the insertable element 118 penetrates the skin surface 148 at an insertion site 152. For example, this insertion site 152 can be arranged substantially at the location of a virtual point of intersection of the insertable element 116 in the rest state, i.e. the non-inserted state, with a plane of the underside 130, provided the insertable element 116 is not deformed or is only inappreciably deformed during the insertion. For example, a deviation of not more than 3 mm can be set, preferably of not more than 1 mm, in order to avoid stresses.

Figure 3:
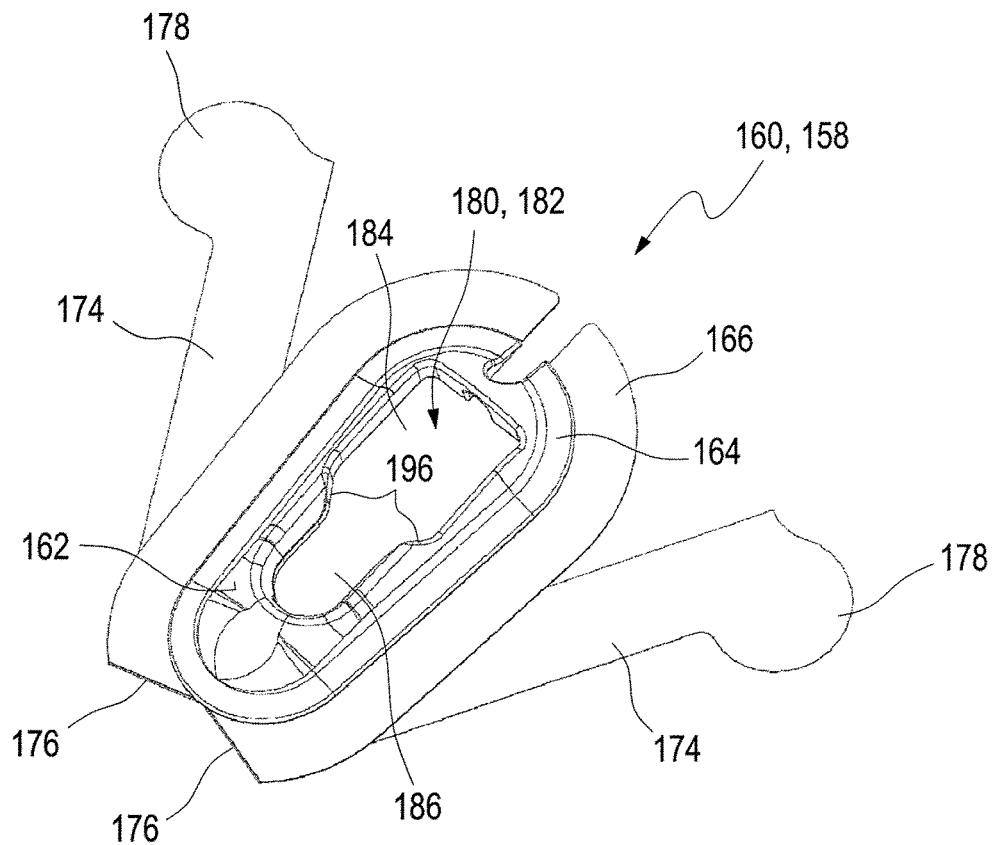
FIGS. 3A and 3B show different views of a protective component.
Figure 3:
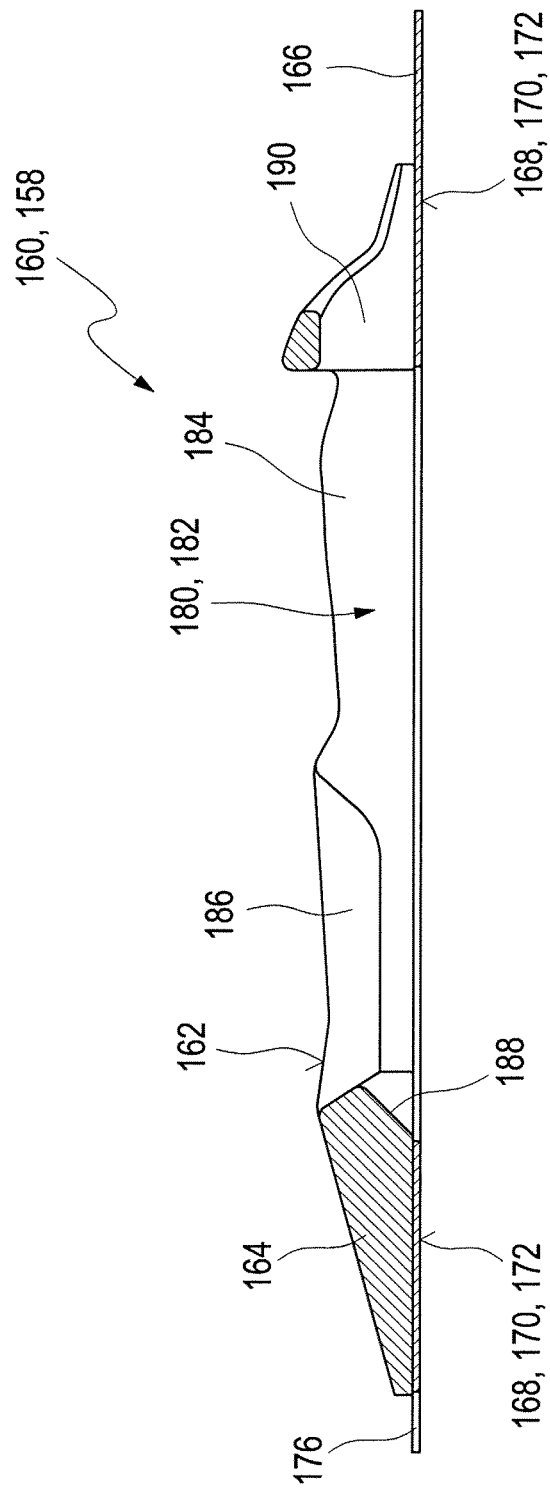

The insertable element 116 and the functional component 114 form a functional assembly 154. As has been described above, the functional component 114 has small dimensions, and is designed relative to the insertion site 152, such that an optimal insertion is possible. However, in the inserted state of the insertable element 116 as shown in FIG. 2B, this gives rise to various problems. Thus, the functional component 114 can shift on the skin surface 148 relative to the insertion site 152, which can lead to painful stresses or even injury in the area of the insertion site 152. Moreover, an insertion area 156 on the skin surface 148, which insertion area 156 is a projection of the insertable element 116 onto the skin surface 148 in the inserted state, and also surrounding adjacent areas are very sensitive to pressure, tension or similar mechanical loads. Mechanical loads of this kind can affect the measurement results of the insertable sensor 118 and/or can be extremely painful. The free accessibility to the insertion site 152, by means of the suitably small design of the functional component 114, has been achieved at the cost of these disadvantages. However, in order to optimally protect the insertion area 156 and the insertion site 152, it is proposed that the functional component 116 is only one part of a multi-part housing 158. Accordingly, a method for protecting the functional assembly 154 is proposed in which the functional assembly 154 is protected by an additional protective component 160. This protective component 160, as part of the multipart housing 158, is shown in different views in FIGS. 3A and 3B. FIG. 3A shows a perspective plan view of a top 162 facing away from the skin surface 148 during operation, and FIG. 3B shows a sectional view through the protective component 160 from the side. As will be seen from the sectional view according to FIG. 3B, the protective component 160 comprises a protective housing 164, on the underside of which a plaster 166 is in turn arranged. Accordingly, at least one contact face 170 is formed on at least one underside 168 of the protective component 160 and is designed as a self-adhesive surface of the protective component 160. For example, in the assembled state of the housing 158, this contact face 170 and this self-adhesive surface 172 can partially enclose or preferably even completely enclose the contact face 132 of the functional component 114. As is shown in FIG. 3, the self-adhesive surface 172 can in turn be protected by one or more liners 174, which are not shown in FIG. 3B. For example, the plaster 166 can in turn have one or more edges 176, at which the liner 174 is bent back and returned parallel to itself, such that one or more pull-off tabs 178, preferably two pull-off tabs 178, are in turn formed. By pulling the pull-off tabs 178 away from the edges 176, the self-adhesive surface 172 of the protective component 160 is exposed and, for example, affixed to a skin surface 148 (not shown in FIGS. 3A and 3B).

Figure 4:
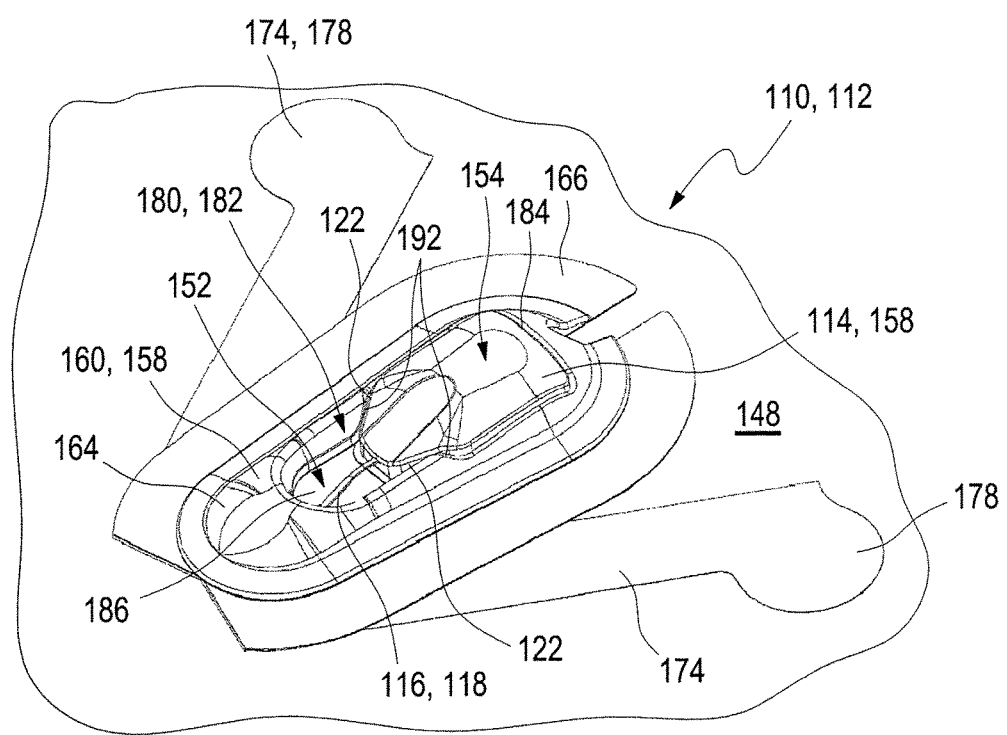
FIG. 4 shows a view of a medical device after the protective component according to FIGS. 3A and 3B has been placed on the functional component according to FIGS. 2A and 2B and before a liner is detached.
Figure 5:
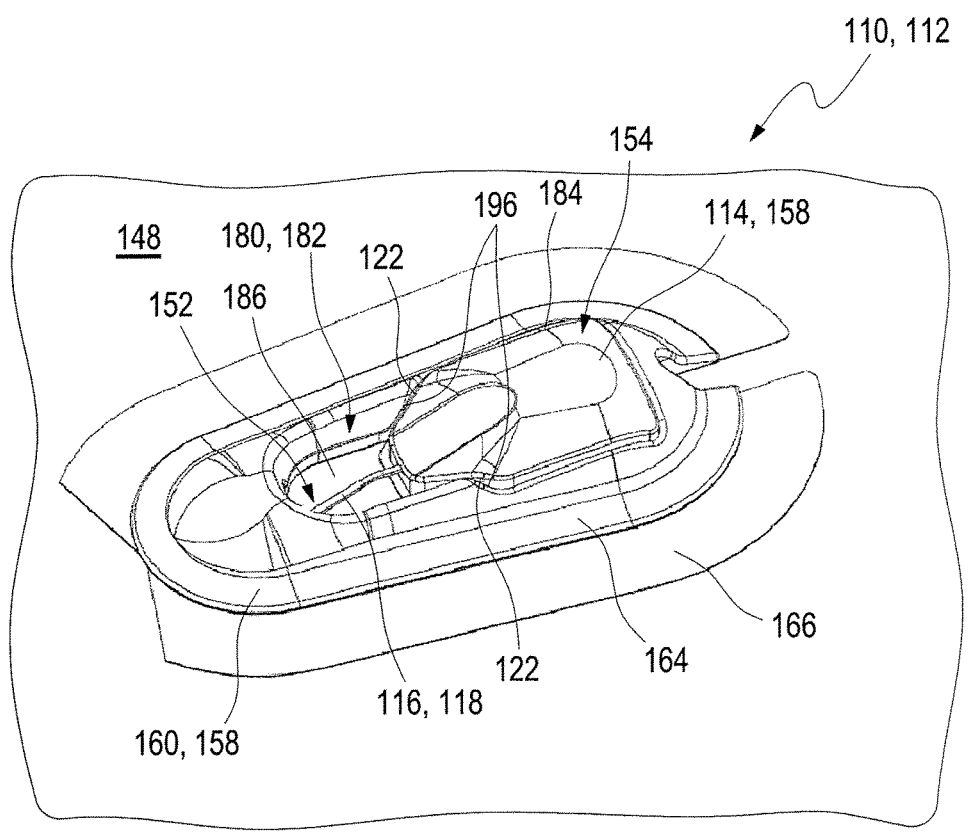
FIGS. 5A and 5B show different views of the medical device according to FIG. 4 after the liner is detached from the protective component.
Figure 5:
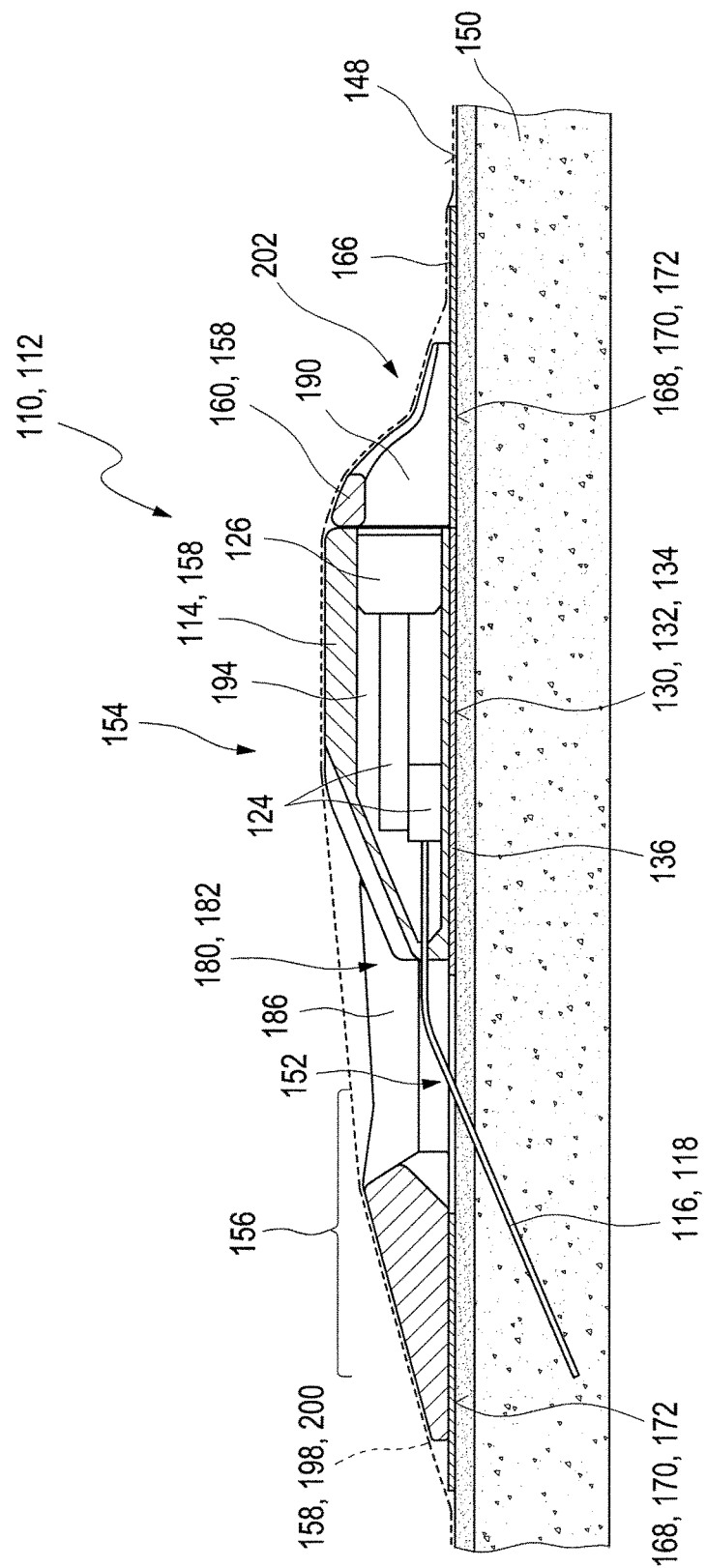

Moreover, the protective component 160 has a seat 180 in the form of an opening 182. In the proposed method for protecting the functional assembly 154, preferably with the element 116 already inserted into the body tissue 150, the protective component 160 is turned back over the functional component 114, with the functional component 114 being fitted into this opening 182. A force-fit and/or form-fit connection can be produced, for example, between the protective component 160 and the functional component 114. This is shown in FIG. 4. In a plan view of the skin surface, the protective component 160 partially or completely encloses the functional component 114 and preferably also the insertion area 156 (not shown in FIG. 4). According to FIGS. 3A and 3B, the opening 182 preferably has a first area 184, in which the functional component 114 is received, for example with a force fit or form fit, and a free space 186 in the area of the insertion site 152. This free space 186 means that, even in the state shown in FIG. 4 in which the protective component 160 is fitted onto the functional component 114 and the functional assembly 154, the insertion site 152 remains accessible and visible from above, for example for visual observation or cleaning. The connection of the protective component 160 to the functional component 114 is preferably reversible, such that, even during the operation of the functional assembly 154, for example in measurement mode, a medical function of the functional assembly 154 is unaffected by a removal of the protective component 160. This can be assisted by various configurations of the protective component 160. For example, as can be seen from FIG. 3B, the opening 182 in the area of the insertable element 116 can have a bevel 188 in proximity to the insertion site 152 or above the insertion area 156. Moreover, as has been explained above, the functional component 114 can have an interface 126 (see FIG. 5B), which can be linked via a cable for example. In the area of this interface 126, the protective component 160 can, for example, have a cable duct 190, for example in the form of a groove which is open downward in the direction of the skin surface 148 and through which a cable or another link to the interface 126 can be routed, such that the protective component 160 can be fitted or removed as and when desired, without affecting the interface 126 and its contact, and thus without having to interrupt the function of the functional assembly 154. The protective component 160 can be fully inert, for example, and can have purely mechanical protective functions. However, as is indicated in FIG. 4, at least one interface 192 can exist between the protective component 160 and the functional component 114 and is closed when these components are connected, such that, for example, an electrical connection can also be established between these components. In this way, one or more parts of the medical device 110 that have a function going beyond a purely mechanical protective function can be integrated in the protective component 160, for example parts for a medication function. Moreover, at least one further insertable element 116 can be provided which, for example, can be connected to the protective component 160, for example a catheter of a medication device.

As can be seen from FIG. 4, the functional assembly 154 is mechanically protected by the fitting of the protective component 160, wherein the protective component 160 covers the functional component 114 and preferably also the insertion area 156 and surrounds these in a ring shape (in this case an oval shape for example). After the protective component 160 has been fitted, the liner 174 can be removed from the self-adhesive surface 172 of the protective component 160 by pulling on the pull-off tabs 178. The contact face 170 of the protective component 160 thus also adheres to the skin surface 148 and surrounds the contact face 132 of the functional component 114, which likewise adheres to the skin surface 148. This state is shown in FIGS. 5A and 5B. FIG. 5A shows a plan view of the arrangement according to FIG. 4 with the liner 174 detached, and FIG. 5B shows a sectional view through the finished medical device 112 placed on the skin surface 148. As has been explained above, it will also be seen here that the functional component 114 can enclose one or more functional modules 124, which can be integrated, for example, in the functional component 114 or can be received inside an interior 194 of the functional component 114. It will also be seen from this sectional view according to FIG. 5B that the insertion area 156 is preferably completely covered by the housing 158, except for the free space 186 above the insertion site 152. The contact face 170 of the protective component 160 surrounds the contact face 132 of the functional component 114 preferably completely. As can be seen from FIG. 5A, the opening 182 of the seat 180 is preferably dimensioned in such a way that the first area 184 is adapted in shape to the outer contour of the functional component 114, such that the latter cannot turn inside the opening 182 and cannot slide inside this opening 182. For this purpose, for example, one or more shoulders 196 can be provided, which cooperate with the beveled edges 122 of the functional component 114 such that the latter cannot slide into the free space 186 and is instead fixed relative to the insertion site 152. Thus, no rotation or shifting inside the opening 182 is possible to any appreciable extent. Both the functional component 114 and also the protective component 160 can be made from suitable materials, preferably from materials that have flexible or deformable properties. In principle, the protective component 160 can be made from a softer material than the functional component 114. Examples of suitable materials are polyurethanes and/or silicones.

It will also be seen from FIG. 5B that the housing 158 can optionally comprise further structural elements. Thus, FIG. 5B indicates that an optional protective covering 198 can also be applied over the entire assembly, which protective covering 198 can likewise be a constituent part of the housing 158 and, for example, can be designed as a self-adhesive transparent plaster 200. The transparent plaster 200 can protrude laterally beyond the protective component 160 and, for example, can also be partially affixed to the skin surface 148. The optional transparency of the transparent plaster 200 also optionally permits observation of the insertion site 152 through the transparent plaster 200 and through the free space 186. The transparent plaster 200 can be exchanged, for example together with the protective component 160, without disrupting the function of the functional assembly 154, and can be removed as and when desired and, for example, replaced. In this way, all the parts of the medical device 110 that are arranged above the skin surface 148 form a base 202 of the medical device 110, which base 202 cooperates with the at least one insertable element 116. For example, the base 202 can be a sensor base. This base 202 comprises the housing 158, which has a multipart design and for example, in addition to the functional component 114, comprises the protective component 160, which can be applied in succession. This ensures an optimal protection of the inserted insertable element 116.

While exemplary embodiments incorporating the principles of this disclosure have been disclosed hereinabove, this disclosure is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

| List of reference signs | |
|---|---|
| 110 | medical device for carrying out at least one function |
| 112 | sensor device |
| 114 | functional component |
| 116 | insertable element |
| 118 | insertable sensor |
| 120 | front face |
| 122 | beveled edges |
| 124 | functional module |
| 126 | interface |
| 128 | top of the functional component |
| 130 | underside of the functional component |
| 132 | contact face of the functional component |
| 134 | self-adhesive surface of the functional component |
| 136 | plaster |
| 138 | liner |
| 140 | edge |
| 142 | pull-off tab |
| 144 | bevel |
| 146 | depression |
| 148 | skin surface |
| 150 | body tissue |
| 152 | insertion site |
| 154 | functional assembly |
| 156 | insertion area |
| 158 | housing |
| 160 | protective component |
| 162 | top of the protective component |
| 164 | protective housing |
| 166 | plaster |
| 168 | underside |
| 170 | contact face of the protective component |
| 172 | self-adhesive surface of the protective component |
| 174 | liner |
| 176 | edges |

-continued

List of reference signs

| | |
|---|---|
| 178 | pull-off tabs |
| 180 | seat |
| 182 | opening |
| 184 | first area |
| 186 | free space |
| 188 | bevel |
| 190 | cable duct |
| 192 | interface |
| 194 | interior |
| 196 | shoulders |
| 198 | protective covering |
| 200 | transparent plaster |
| 202 | base |

What is claimed is:

1. A medical device for carrying out at least one medical function, comprising:
    an insertable element that can be at least partially inserted into a body tissue of a user at an insertion site at which the insertable element passes through the skin surface of the user; and
    a housing adapted for placement on a skin surface of the user, the housing comprising:
        a functional component comprising an electronic module configured to control the insertable element, the functional component being connectable to the insertable element; and
        a protective component that is connectable to the functional component and wherein the functional component and the protective component each have a self-adhesive surface adapted to contact the skin surface;
        wherein, when the protective component is connected to the functional component, the protective component at least partially surrounds the functional component and the housing defines a free space for access to the insertion site from above.

2. The medical device of claim 1, wherein, when the protective component is connected to the functional component and positioned on the skin surface, the insertion site is completely surrounded by the housing.

3. The medical device of claim 1, wherein an outer edge of the protective component is adapted to completely enclose a projection of the functional component and of the insertable element onto the skin surface of the user.

4. The medical device of claim 1, wherein, when the protective component is connected to the functional component and positioned on the skin surface, the insertion site is arranged substantially centrally with respect to a contact face of the housing.

5. The medical device of claim 1, wherein the insertable element comprises a sensor for detection of at least one analyte in a body fluid or an insulin pump.

6. The medical device of claim 1, wherein at least one function of the functional component remains operable when the functional component is disconnected from the protective component.

7. The medical device as claimed in claim 6, wherein the at least one function of the functional component comprises an analysis of a body fluid that can be performed by the functional component in cooperation with the insertable element.

8. The medical device of claim 7, wherein the medical function further comprises delivering medication.

9. The medical device of claim 1, wherein the housing is flexible.

10. The medical device of claim 1, wherein the insertable element is connectable to one side of the functional component, wherein the functional component has at least one depression facing toward the one side.

11. The medical device of claim 1, wherein the housing further comprises a protective cover that at least partially covers the protective component and the functional component on a side of the housing that is adapted to face away from the skin surface.

12. The medical device of claim 1, wherein, when the protective component is connected to the functional component, the functional component is configured to cooperate mechanically, electrically or fluidically with the insertable element.

13. The medical device as claimed in claim 1, wherein the protective component has a seat with an opening configured to receive the functional component.

14. The medical device of claim 1, wherein the protective component is connectable to the functional component with a form fit and/or force fit.

15. The medical device of claim 1, wherein the protective component has an opening into which the functional component is configured to be completely or partially fitted.

16. The medical device of claim 15, wherein the shape of the opening corresponds to an outer shape of the functional component.

17. A method of using a medical device having an insertable element and a functional component that is connectable to the insertable element, the method comprising:
    connecting the insertable element to the functional component;
    connecting a protective component to the functional component and at least partially surrounding the functional component with the protective component;
    inserting the insertable element at least partially into the skin of a user at an insertion site;
    adhering the protective component directly to the skin surface and adhering the functional component directly to the skin surface of the user;
    providing a free space with the housing for access to the insertion site from above; and
    carrying out at least one medical function on the user with the medical device.

18. The method of claim 17, wherein the medical function comprises detection of at least one analyte in a body fluid or infusing insulin.

19. The method of claim 17, further comprising connecting the protective component to the functional component after the step of inserting of the insertable element.

20. The method of claim 17, wherein, after the protective component is connected to the functional component, the protective component borders the functional component.

21. The method of claim 20, further comprising completely surrounding the functional component with the protective component.

22. A medical device for carrying out at least one medical function, comprising:
    an insertable element that can be at least partially inserted into a body tissue of a user; and
    a housing adapted for placement on a skin surface of the user, the housing comprising:
        a functional component comprising an electronic module for the insertable element, the functional component being connectable to the insertable element; and a protective component configured to at least partially enclose the functional component, wherein the protective component is connectable to the functional component and wherein the functional component and the protective component each have a self-adhesive surface adapted to contact the skin surface;

wherein, the functional component is operable for analysis of a body fluid when the functional component is disconnected from the protective component.

23. A method of using a medical device having an insertable element and a functional component that is connectable to the insertable element, the method comprising:

connecting the insertable element to the functional component;

connecting a protective component to the functional component and at least partially surrounding the functional component with the protective component;

inserting the insertable element at least partially into the skin of a user at an insertion site;

adhering the protective component directly to the skin surface and adhering the functional component directly to the skin surface of the user;

carrying out at least one analysis of a body fluid; and maintaining operation of the functional component for analysis of the body fluid when the functional component is disconnected from the protective component.

* * * * *